United States Patent
Asaff Arancibia et al.

(10) Patent No.: US 9,815,761 B2
(45) Date of Patent: Nov. 14, 2017

(54) METHOD FOR EXTRACTING FERULIC ACID AND/OR ITS SALTS

(71) Applicant: LABORATORIOS MINKAB, Tlalnepantla (MX)

(72) Inventors: Jorge Selim Asaff Arancibia, Zapopan (MX); Angel Emilio Aceves Diez, Zapopan (MX); Ruben Herrera Herrera, Zapopan (MX); Maria Lucia Alejo Castillo, Zapopan (MX)

(73) Assignee: LABORATORIOS MINKAB, Tlalnepantla (MX)

( * ) Notice: Subject to any disclaimer, the term of this patent is extended or adjusted under 35 U.S.C. 154(b) by 0 days.

(21) Appl. No.: 14/782,003

(22) PCT Filed: Nov. 21, 2014

(86) PCT No.: PCT/MX2014/000186
§ 371 (c)(1),
(2) Date: Oct. 2, 2015

(87) PCT Pub. No.: WO2016/085317
PCT Pub. Date: Jun. 2, 2016

(65) Prior Publication Data
US 2016/0311749 A1    Oct. 27, 2016

(51) Int. Cl.
C07C 51/47    (2006.01)
C07C 51/43    (2006.01)
C07C 51/41    (2006.01)
C07C 51/42    (2006.01)
C07C 59/13    (2006.01)

(52) U.S. Cl.
CPC .............. *C07C 51/47* (2013.01); *C07C 51/41* (2013.01); *C07C 51/42* (2013.01); *C07C 51/43* (2013.01); *C07C 59/13* (2013.01)

(58) Field of Classification Search
None
See application file for complete search history.

(56) References Cited

FOREIGN PATENT DOCUMENTS

| CN | 102908371 A | 2/2013 |
| WO | 2004110975 A1 | 12/2004 |
| WO | 2014119990 A1 | 8/2014 |

OTHER PUBLICATIONS

Machine English Translation of Torres et al. (WO 2004110975).*

* cited by examiner

*Primary Examiner* — Sudhakar Katakam
*Assistant Examiner* — Jennifer C Sawyer
(74) *Attorney, Agent, or Firm* — Harness, Dickey & Pierce, P.L.C.

(57) ABSTRACT

Method for extracting ferulic acid and/or its salts from a previously conditioned source rich in ferulic acid and its salts which comprises adsorbing the ferulic acid and/or its salts on a column packed with synthetic resin, desorbing the ferulic acid and/or its salts using an organic solvent, separating the liquor rich in ferulic acid into two fractions according to their water content, separately concentrating the two liquor fractions, mixing and concentrating said fractions, adding 2 volumes of water to them, concentrating the mixture obtained, separating out the insoluble impurities by sedimentation, pre-crystallizing the ferulic acid and/or its salts with a synthetic purification resin, crystallizing out the ferulic acid and/or its salts, separating the ferulic acid and/or its salts from the crystallization mother liquors and drying it and screening it.

15 Claims, No Drawings

METHOD FOR EXTRACTING FERULIC ACID AND/OR ITS SALTS

CROSS-REFERENCE TO RELATED APPLICATIONS

This application is a 371 U.S. National Stage of International Application No. PCT/MX2014/000186, filed Nov. 21, 2014. The disclosures of the above application is incorporated herein by reference.

TECHNICAL FIELD OF THE INVENTION

This invention preferably relates to the technical field of chemistry, food, cosmetics and pharmaceuticals, given that it provides a method for the extraction of ferulic acid and/or its salts from a source rich in ferulic acid and/or its salts. It also provides the products obtained by said method, which include ferulic acid and its salts, which may be useful in the food, cosmetics, chemical and pharmaceutical industries, among others, and a source which is low in or free from ferulic acid and/or its salts, which can be reused or discharged to the environment without fear of pollution.

BACKGROUND TO THE INVENTION

Ferulic acid is a very abundant compound in nature as it is a component of the cell wall of many plant species such as rice, maize and sugar beet, among others. However it is not found in the free form, but forms glucoside links to the carbohydrate chains of the cell wall as a result of which both enzyme and alkaline hydrolytic methods are used to release it. For example, an enzyme method for obtaining free ferulic acid is described in patent document U.S. Pat. No. 6,143,543.

Patent application WO2004/110975 describes a process for the recovery of ferulic acid in free form from the water used to cook maize known as nejayote resulting from the nixtamalization industry. This process comprises acidifying the nejayote (>pH 4) with a dilute solution (20 to 35%) of sulfuric acid, hydrochloric acid or phosphoric acid to encourage the adsorption of ferulic acid. The ferulic acid is adsorbed with activated carbon, although synthetic resins such as amberlite, polypyrrolidone and divinylbenzene styrene may also be used; this stage can be carried out in a tank with stirring or semi-continuously in packed columns.

When carried out in a stirred tank, stirring takes place at between 100 and 150 rpm for 1 to 8 hours or until ferulic acid adsorption is more than 95%, depending upon the particle size and density of the adsorbent material, at an operating temperature of 20 to 50° C. The adsorbent material is recovered by filtering, settling or centrifuging and is deposited in the desorption column, in which it is subsequently washed with water acidified to a pH of less than 4 in order to remove the suspended solids retained.

When using packed columns, the acidified nejayote is filtered or centrifuged to remove suspended solids before being passed through the column. The operating temperature is from 20 to 50° C.; the velocity of the liquid varies between 3 and 8 volumes of packed bed per hour, with an end point fixed at a ferulic acid concentration in the effluent of not more than 5% of its initial concentration in the nejayote.

The adsorbed ferulic acid is recovered by desorption or elution with organic solvents such as ethanol or ethyl acetate. The elution temperature is between 50 and 70° C. The solvent is recycled through the column and its volume is equal to the free space of the packed column, which is between 25 and 40% of the bed depending upon the nature of the adsorbent material; the recycling time is between and 40 minutes, with 4 to 6 desorption cycles with fresh solvent.

The solvent is removed by evaporation, leaving a solid residue containing 65 to 95% of ferulic acid, depending upon the solvent used. The crude ferulic acid can be purified by recrystallization, gradually reducing the polarity of a concentrated solution in ethyl acetate by adding low polarity organic solvents such as methyl chloride and hexane, or by reducing the pH of an aqueous alkaline solution.

Patent document CN101845464 discloses a method for preparing ferulic acid from maize grains hydrolyzed by a multi-purpose enzyme. The method comprises steeping maize grains in NaOH in the dark, sterilizing at high pressure, adding a multi-purpose enzyme with peptidase and esterase activities to hydrolyze ester and peptide bonds in the cell wall, obtaining a supernatant by centrifuging, treating the supernatant in a chromatography column, eluting the concentrate obtained by extraction with ethyl acetate and obtaining ferulic acid through the use of a rotary evaporator.

Among the disadvantages encountered with the above-mentioned processes there is the fact that the removal of suspended solids is partial and the remaining suspended solids cause the adsorbent material to become fouled and degraded, making it difficult to regenerate and reuse, increasing operating costs because this adsorbent material has to be disposed of.

Active carbon has a very short useful life, so large quantities of the material are required in order to implement a process using activated carbon on an industrial scale, and it has to be periodically replaced, thus increasing operating cost.

Another disadvantage is that carrying out desorption through recycling cycles is not the most suitable way because in the desorption process the material is transferred by a concentration gradient, and for this elution has to be performed continuously (input to output) without recycling, as this is the most efficient way of removing ferulic acid. Likewise the desorption suggested in the documents mentioned above is carried out at a temperature of 50 to 70° C., which involves an additional operating cost to raise and maintain the temperature of the solvent during the operation.

In these methods there is also no mention of separation of the impurities accompanying the ferulic acid, and these reduce the degree of purity of the final product. A greater number of purification steps are required in order to increase purity.

Another disadvantage of the prior art is that there is no handling and final disposal of the deferulized nejayote, the flows of water used for cleaning and regeneration of the adsorbent medium and the crystallization mother liquors; as a result of this all these effluents produced result in a loss of water.

Because of the abovementioned disadvantages, a method has been developed to obtain ferulic acid and/or its salts, and this is described below.

DETAILED DESCRIPTION OF THE INVENTION

The characteristic details of this invention are clearly demonstrated in the following description and its accompanying examples included by way of illustration, but they should not be regarded as limiting the invention.

The method according to this invention preferably starts from a source rich in ferulic acid which has previously been conditioned by means of conventional conditioning procedures. To cite an example, by document MX2013000943 discloses a continuous, semi-continuous or batch method for preparing or conditioning effluents from the nixtamalization process commonly known as nejayote, by removing or eliminating suspended solids (TSS), in which the method comprises: (i) adding acid substances (hydrochloric acid, sulfuric acid and/or phosphoric acid or any of its acid salts (monobasic sodium or potassium phosphate) to the nejayote in order to acidify it to a pH of 4 to 6.5, preferably 5 to 6; (ii) adding hydrolase enzymes to the nejayote in a quantity depending upon its starch content and the desired hydrolysis time, such as exoglucanases, endoglucanases, β-glucosidases, preferably α-amylase, β-amylase and/or glucoamylases; (iii) incubating the above mixture at between 20 and 90° C., preferably between 50 and 80° C., for 30 seconds to 90 minutes, preferably 5 to 30 minutes; (iv) adding a cationic flocculating agent (non-toxic polyacrylamides) to the hydrolyzed nejayote in a concentration of between 5 and 100 ppm, preferably between 15 and 50 ppm, for 10 to 120 minutes, preferably 30 to 60 minutes; and (v) separating out the flocculated material by either sedimentation, filtration, sifting or screening, centrifuging and/or flotation.

Said document MX2013000943 also discloses an effluent free from suspended solids (TSS) obtained by the above-mentioned method in which said effluent comprises between 0 and 30 ppm of TSS, between 5 and 18 g/L of dissolved solids and between 0.5 and 1.5 g/L of phenolic compounds, and has a pH of between 4 and 6.5.

A source rich in ferulic acid and/or its salts is a substance containing ferulic acid and/or its salts in a concentration varying between preferably 0.2 and 2.5 g/L. Some examples of liquid substances rich in ferulic acid and its salts may be the nejayote resulting from the nixtamalization of maize, or any other liquid which is useful in processes for extracting ferulic acid and its salts.

When referring to ferulic acid, we are also referring to its salts, which may be present in the source rich in that acid.

The ferulic acid and/or its salts obtained by the process according to this invention may be used as a supplement in other products, such as foods, cosmetics, chemicals and medicinal products, among others. These products supplemented with said ferulic acid and/or its salts fall within the scope of this invention.

The method according to this invention begins by submitting the source rich in ferulic acid and its salts, already conditioned and free of suspended solids, to adsorption. Adsorption may be carried out using any type of packed column, preferably columns packed with a synthetic resin having affinity (SR). Here the synthetic resin is selected from the following group: Amberlite XAD-4, Amberlite XAD-16, PVPP (polyvinyl polypyrrolidone), DVBS (divinylbenzene styrene), DVBPS (divinylbenzene polystyrene resins), preferably polyvinyl benzyl dimethyl amine, Hypersol-Macronet® (polyvinyl benzyl dimethyl amine (a cross-linked polystyrene matrix)).

After this stage the source of ferulic acid and/or its salts is low in or free from ferulic acid, and may also be regarded as a deferulized effluent or one free from ferulic acid and/or its salts, more specifically as deferulized nejayote. This deferulized effluent is characterized in that it contains 8000 to 13000 mg/L of total dissolved solids and 10 to 100 mg/L of a phenolic fraction; it has a pH of 4.5 to 5.5.

This deferulized effluent may be reused in subsequent nixtamalization processes, for example, forming all or part of the nixtamalization solution, which results in a saving of water in these nixtamalization processes. On the other hand this deferulized source may be placed in the environment following additional treatment to remove the remaining organic and inorganic load, either by evaporation or reverse osmosis, thus complying with environmental standards. Thus this treated or deferulized source obtained up to this part of the method according to this invention forms part of the scope of this invention.

For its part the ferulic acid and/or its salts which adhere to the synthetic resin are desorbed from the synthetic resin to ferulic acid and/or its salts using a solvent in order to recover them. Here the desorption takes place directly in the packed column with a counter-current flow of solvent in a concentration of preferably from 80 to 96% v/v. A liquor rich in ferulic acid and/or its salts is obtained in this stage.

An organic solvent selected from the following group is preferred: straight-chain hydrocarbons, cyclic hydrocarbons, aliphatic alcohols, aromatic alcohols, aldehydes, ketones, acid esters and/or combinations thereof. It is even more preferred that the organic solvent be an aliphatic alcohol, for example ethanol.

Depending on how the desorption is performed, liquor rich in ferulic acid and/or its salts is separated out in two fractions according to the amount of water which they contain. Here one fraction is low in solvent and rich in water, its water content being 50 to 70%, while the other fraction is rich in solvent and low in water, with a water content of approximately 5 to 10%.

The liquor is separated into two fractions in order to recover the high purity alcohol, which can be used in subsequent desorptions without the need for distillation, thus favoring the economics of the process. The efficiency of recovery of the phenolic compounds fraction (PCF) in the desorption stage is 98%.

The adsorption resin is then washed with water acidified to 1%, and then regenerated with a 1% solution of soda, leaving it ready for the next absorption and desorption cycle.

The two liquor fractions are concentrated separately to 3.5 or 3.7 times their initial concentration. These are subsequently mixed together and finally concentrated to 2.5 to 3 times the initial volume of the mixture. Concentration may take place by evaporation at a temperature of 60 to 90° C., with or without vacuum.

2 volumes of water are then added to the concentrated mixture, and it is subsequently concentrated to approximately 1.7 times its initial concentration. This concentrated mixture is cooled to 20 to 40° C. and allowed to stand for 1 hour in order to separate out the insoluble impurities by sedimentation. Once free of insoluble impurities the mixture is reheated to 80° C. and passed through a synthetic purification resin which may be Amberlite XAD-4, Amberlite XAD-16, PVPP (polyvinyl polypyrrolidone), DVBS (divinylbenzene styrene), DVBPS (divinylbenzene polystyrene resins) and Amberlite FPX66. Up to this part of the process there is pre-crystallization of the impurities present in the mixture.

In order to crystallize out the ferulic acid and/or its salts the remaining solvent (alcohol) is removed by evaporation from the mixture with reduced impurities obtained in the previous step, concentrating its volume by half. The resulting mixture is transferred to a crystallizing container with a cooling jacket. Here the ferulic acid and/or its salts precipitate out after standing for 4 hours at a temperature of approximately 21° C., with a purity of 80 to 90% being obtained.

Free crystals of ferulic acid and/or its salts are separated out from the crystallization mother liquors by centrifuging. Here the centrifuging medium may be a conventional crystal centrifuge at 1000 rpm for approximately 30 minutes. As a result of this the final moisture content of the crystals will be approximately 30%.

It should be pointed out that the crystallization mother liquors obtained in this stage may be reutilized in subsequent crystallizations.

The crystallized ferulic acid and/or its salts are dried in drying equipment under vacuum and an inert atmosphere for 2 hours, until a moisture content of less than 1% is obtained.

Finally the dry ferulic acid and/or its salts are screened and packed.

EXAMPLES

One of the preferred means for performing the method for recovering ferulic acid and/or its salts according to this invention is illustrated below through the following examples.

Example 1

Recovery of Ferulic Acid and its Salts from Previously Conditioned Nejayote 250 m$^3$ of nejayote originating from the nixtamalization of maize was used, this nejayote having previously been conditioned through the process described in patent document MX2013000943. The principal characteristics of this conditioned nejayote were measured and the results are shown in Table 1.

TABLE 1

Main characteristics of previously conditioned nejayote.

| Characteristic | Value | Units |
|---|---|---|
| Temperature | 35 | ° C. |
| pH | 5.0 | — |
| Viscosity | 2.0 | cPoise |
| Total suspended solids (TSS) | 0.0 | mg/L |
| Total dissolved solids (TDS) | 16,000 | mg/L |
| Phenolic fraction (PCF) | 1,700 | mg/L |
| Free ferulic acid (FFA) | 600 | mg/L |
|  | 150 | Kg |

The concentration of the phenolic fraction (PCF) includes ferulic acid and its salts, molasses and other minority phenolic compounds linked to sugars. Adsorption of the conditioned liquid source was carried out using a column packed with a Hypersol-Macronet® polyvinyl benzyl dimethyl amine (cross-linked polystyrene matrix) synthetic resin (SR) having affinity.

The synthetic resin having affinity was cleaned and regenerated using water acidified to 1% and regenerated with a 1% soda solution.

The (deferulized) nejayote free of phenolic fraction was intended for reuse in processes for the nixtamalization of maize. Meanwhile the ferulic acid adsorbed on the resin having affinity was recovered by the process of extraction proposed in this invention. The balance of dissolved solids in the adsorption process is shown in Table 2.

TABLE 2

Dissolved solids in the adsorption process.

| Characteristic | Units | Conditioned nejayote | Deferulized nejayote |
|---|---|---|---|
| Total suspended solids (TSS) | mg/L | 0.0 | 0.0 |
| Total dissolved solids (TDS) | mg/L | 16,000 | 11,000 |
| Phenolic fraction (PCF) | mg/L | 1,700 | 51.0 |
|  | Kg | 425 | 12.75 |

The recovery efficiency of PCF in the adsorption stage was 97%.

22 m$^3$ of 94% v/v ethanol were used in the desorption of ferulic acid with counter-current flow. A liquor rich in ferulic acid and/or its salts, accompanied by molasses and other minority phenolic compounds, both free and linked to sugars, was obtained; in the course of the desorption this was separated into two fractions according to their water content, the values of which are shown in Table 3. Here fraction 1 was rich in water, while fraction 2 was rich in alcohol and low in water.

The liquor was separated into two fractions in order to recover the high purity alcohol and this was reused in subsequent desorptions without the need for distillation, thus favoring the economics of the process. The recovery efficiency of PCF in the desorption stage was 98%.

TABLE 3

Desorption values

| Characteristic | Units | Fraction 1 | Fraction 2 |
|---|---|---|---|
| Volume | L | 12,600 | 15,400 |
| Temperature | ° C. | 25 | 25 |
| Absolute density |  | 0.93 | 0.82 |
| Alcohol content | % v/v | 48 | 90 |
| Water content | % v/v | 52 | 10 |
| Phenolic fraction (PCF) | mg/L | 20,500 | 9,500 |
|  | Kg | 258.3 | 146.3 |

Fractions 1 and 2 were concentrated up to 3.7 times their initial concentration, and the values for this may be seen in Table 4.

As a result of separation of the fractions the recovery efficiency for alcohol at 94% v/v was 48% and it was only necessary to distill 52% of the 22 m$^3$ of alcohol used for desorption.

TABLE 4

Values obtained from fractions 1 and 2, concentrated up to 3.7 times their initial concentration.

| Characteristic | Units | Concentrated fraction 1 | Concentrated fraction 2 |
|---|---|---|---|
| Volume | L | 3,405 | 4,162 |
| Evaporation temperature | ° C. | 55 | 48 |
| Evaporation pressure | mm Hg | 450 | 470 |
| Alcohol content | % v/v | 5.0 | 84.0 |
| Water content | % v/v | 95.0 | 16.0 |
| Phenolic fraction (PCF) | mg/L | 75,850 | 35,150 |
|  | Kg | 258.3 | 146.3 |

These concentrated fractions were then pooled, and the mixture was concentrated to 2.5 times its initial volume (CM1) by evaporation to 80° C., and the values for this are shown in Table 5.

TABLE 5

Values obtained from mixture of fractions 1 and 2, and the concentrate from that mixture (CM1).

| Characteristic | Units | Fractions 1 + 2 | (CM1) |
|---|---|---|---|
| Volume | L | 7,567 | 3,027 |
| Alcohol content | % v/v | 48 | 10 |
| Water content | % v/v | 52 | 90 |
| Phenolic fraction (PCF) | mg/L | 53,465 | 133,663 |
|  | Kg | 404.6 | 404.6 |

In order to pre-crystallize the molasses and minority phenolic compounds the previously concentrated mixture was mixed with two volumes of water; it was then again concentrated to 1.7 times its initial concentration (CM2). See Table 6.

TABLE 6

Pre-crystallization values.

| Characteristic | Units | CM1 and water | Concentrated mixture (CM2) |
|---|---|---|---|
| Volume | L | 9,081 | 5,342 |
| Alcohol content | % v/v | 8.3 | 1.8 |
| Water content | % v/v | 91.7 | 98.2 |
| Phenolic fraction (PCF) | mg/L | 44,554 | 75,742 |
|  | Kg | 404.6 | 404.6 |

Said concentrated mixture (CM2) was cooled to 40° C. and allowed to stand for around 1 hour in order to separate out the insoluble impurities such as molasses by sedimentation. The molasses- and insoluble impurities-free mixture was reheated to 80° C. and passed through a synthetic purification resin of the Amberlite FPX66 type, and the values for this are illustrated in Table 7.

TABLE 7

Values for the concentrated mixture (CM2) obtained after sedimentation and passage through the resin.

| Characteristic | Units | CM2 after sedimentation |
|---|---|---|
| Volume | L | 5,300 |
| Phenolic fraction (PCF) | mg/L | 20,000 |
|  | Kg | 106.0 |

In order to crystallize the ferulic acid and its salts the remaining alcohol was eliminated from the mixture obtained in the previous step by evaporation, concentrating its volume by half. Subsequently the resulting mixture was transferred into a crystallizing container with a cooling jacket (see Table 8).

TABLE 8

Results obtained after crystallization.

| Characteristic | Units | Crystallization mixture | Mother liquors |
|---|---|---|---|
| Volume | L | 2,650 | 2,620 |
| Phenolic fraction (PCF) | mg/L | 40,000 | 3,250 |
| Free ferulic acid | mg/L | 30,800 | 40 |
| Other phenolic compounds | mg/L | 9,200 | 3,160 |

The free ferulic acid (FFA) was crystallized out for 4 hours at a temperature of 21° C. Free ferulic acid crystals were separated out from the crystallization mother liquors in a basket centrifuge at 1000 rpm for 30 minutes. The final moisture content of the crystals was 30%.

The crystallization mother liquors were reused in subsequent crystallizations.

The crystals of ferulic acid and its salts were dried in drying equipment under vacuum and an inert atmosphere for 2 hours. The characteristics of the ferulic acid crystals after the drying process are shown in Table 9.

TABLE 9

Characteristics of the ferulic acid crystals after the drying process

| Characteristic | Units | FFA crystals |
|---|---|---|
| Quantity | Kg | 98.0 |
| Purity | % | 83.2 |
| Moisture content | % | 0.5 |

Finally the now dry ferulic acid and its salts were screened in a conventional screening device for subsequent packaging.

According to this example the overall recovery efficiency for FFA using the method described was 68%, using the quantities of pure free ferulic acid in the previously conditioned rich source as a basis for calculation.

The invention claimed is:

1. A method for extracting ferulic acid and/or its salts from a previously conditioned source rich in ferulic acid and/or its salts free from suspended solids; the method comprises:
   i) adsorbing the ferulic acid and/or its salts in a column packed with a synthetic resin having affinity;
   ii) separating out the liquid fraction which is left with a reduced content of ferulic acid and/or its salts from the packed column containing the adsorbed ferulic acid;
   iii) desorbing the ferulic acid and/or its salts from the packed column with a counter-current flow of organic solvent in order to obtain a concentrated liquor of ferulic acid and/or its salts;
   iv) separating the concentrated liquor of ferulic acid and/or its salts into two fractions according to their water content; one fraction containing 50 to 70% of water, and the other only 5 to 10% of water;
   v) separately concentrating the two liquor fractions from 3.5 to 3.7 times their initial concentration;
   vi) pooling the two liquor fractions from the previous stage together;
   vii) concentrating the mixture from the previous stage from 2.5 to 3 times its initial volume by evaporation at 60-90° C.;
   viii) adding 2 volumes of water to the concentrated mixture from the previous stage;
   ix) concentrating the above mixture to about 1.7 times its initial concentration;
   x) separating out the insoluble impurities by sedimentation, allowing the above mixture to cool to about 20 to 40° C. and leaving it to stand for about 1 hour;
   xi) reheating the above mixture to 80° C.;
   xii) removing soluble impurities present in the above mixture by passing the mixture through a synthetic purification resin;
   xiii) crystallizing out the ferulic acid and/or its salts, removing the remaining solvent by evaporation from the mixture from the previous step, concentrating its volume by half, and transferring the resulting mixture into a crystallizing container with a cooling jacket, in which the ferulic acid and/or its salts precipitate out after standing for around 4 hours at 21° C., with a purity of 80 to 90% being obtained;

xiv) separating out the crystals of free ferulic acid and/or its salts from the crystallization mother liquors by centrifuging;

xv) drying the crystals of ferulic acid and/or its salts with drying equipment under vacuum and an inert atmosphere for around 2 hours until a moisture content of less than 1% is obtained; and xvi) screening the already dry ferulic acid and/or its salts.

2. The method as claimed in claim 1, wherein the source rich in ferulic acid and/or its salts contains a concentration of ferulic acid and/or its salts varying between 0.2 and 2.5 g/L.

3. The method as claimed in claim 1, wherein the synthetic resin having affinity is selected from the group: Amberlite XAD-4, Amberlite XAD-16, PVPP (polyvinyl polypyrrolidone), DVBS (divinylbenzene styrene), DVBPS (divinylbenzene polystyrene resins), polyvinyl benzyl dimethyl amine, Hypersol-Macronet® (polyvinyl benzyl dimethyl amine (cross-linked polystyrene matrix)).

4. The method as claimed in claim 3, wherein the synthetic resin having affinity is Hypersol-Macronet® of polyvinyl benzyl dimethyl amine (cross-linked polystyrene matrix).

5. The method as claimed in claim 1, wherein the concentration of organic solvent is 80 to 96% v/v.

6. The method as claimed in claim 1, wherein the organic solvent is selected from the following group: straight-chain hydrocarbons, cyclic hydrocarbons, aliphatic alcohols, aromatic alcohols, aldehydes, ketones, acid esters, and/or combinations thereof.

7. The method as claimed in claim 6, wherein the organic solvent is an aliphatic alcohol.

8. The method as claimed in claim 7, wherein the aliphatic alcohol is an ethanol.

9. The method as claimed in claim 1, wherein the fraction of the liquor rich in water contains 52% of water, while the fraction low in water contains about 10% of water.

10. The method as claimed in claim 1, wherein the concentration of the two liquor fractions is 3.7 times their initial concentration.

11. The method as claimed in claim 1, wherein the concentration in stage vii) is 2.5 times its initial volume and takes place by evaporation at 80° C.

12. The method as claimed in claim 1, wherein the temperature in stage x) is 40° C.

13. The method as claimed in claim 1, wherein the synthetic purification resin is selected from the group: Amberlite XAD-4, Amberlite XAD-16, PVPP (polyvinyl polypyrrolidone), DVBS (divinylbenzene styrene), DVBPS (divinylbenzene polystyrene resins) and Amberlite FPX66.

14. The method as claimed in claim 13, wherein the synthetic purification resin is Amberlite FPX66.

15. The method as claimed in claim 1, wherein the centrifuging in stage xiv) uses a basket centrifuge at 1000 rpm for 30 min, with the result that the moisture content of the crystals is 30%.

* * * * *